(12) United States Patent
Bae et al.

(10) Patent No.: US 7,538,210 B2
(45) Date of Patent: May 26, 2009

(54) SUCROSE-INDUCIBLE PROMOTER FROM SWEETPOTATO

(75) Inventors: Jung Myung Bae, Seoul (KR); Man Sup Kwak, Seoul (KR); Seol Ah Noh, Seoul (KR); Jeong Sheop Shin, Seoul (KR); Shin Woo Lee, Jinju-si (KR)

(73) Assignee: Korea University Industry and Academy Cooperation Foundation (KR)

( * ) Notice: Subject to any disclaimer, the term of this patent is extended or adjusted under 35 U.S.C. 154(b) by 358 days.

(21) Appl. No.: 10/574,842

(22) PCT Filed: Aug. 25, 2005

(86) PCT No.: PCT/KR2005/002820

§ 371 (c)(1),
(2), (4) Date: Apr. 6, 2006

(87) PCT Pub. No.: WO2006/028332

PCT Pub. Date: Mar. 16, 2006

(65) Prior Publication Data

US 2006/0288452 A1    Dec. 21, 2006

(30) Foreign Application Priority Data

Sep. 6, 2004    (KR) .................. 10-2004-0070820

(51) Int. Cl.
C12N 15/82    (2006.01)
C12N 15/11    (2006.01)
C07H 21/04    (2006.01)
C12N 15/00    (2006.01)

(52) U.S. Cl. .................. 536/24.1; 536/23.1; 435/320.1; 435/440; 435/468; 800/287; 800/278

(58) Field of Classification Search .................. None
See application file for complete search history.

(56) References Cited

U.S. PATENT DOCUMENTS

2003/0167518 A1    9/2003    Yeh et al.

OTHER PUBLICATIONS

Kim et al 1994, Plant Molecular Biology 24:105-117.*
Donald et al 1990, EMBO J. 9:1717-1726.*
Dolferus et al 1994, Plant Physiology 105:1075-1087.*
Siedlecka et al 2003 In Planta 217:184-192.*
A. Siedlecka, et al., "The small subunit ADP-glucose pyrophosphorylase (ApS) promoter mediates okadaic acid-sensitive uidA expression in starch-synthesizing tissues and cells in Arabidopsis", *In: Planta*, 2003, vol. 217, No. 2, pp. 184-192.
X Li, et al., "Sucrose regulation of ADP-glucose pyrophosphorylase subunit genes transcript levels in leaves and fruits", *In: Plant Science*, 2002, vol. 162, No. 2, pp. 239-244.
C.H. Harn, et al., "Presence of multiple cDNAs encoding an isoform of ADP-glucose pyrophosphorylase large subunit from sweet potato and characterization of expression levels", *In: Plant Cell Physiology*, 2000, vol. 41, No. 11, pp. 1235-1242.
J.M. Bae, et al., "Molecular cloning and characterization of two novel isoforms of the small subunit of ADP-glucose pyrophosphorylase from sweet potato", *In: Mol. Gen. Genet.*, 1997, vol. 254, No. 2, pp. 179-185.
B. Müller-Röber, et al., "A Truncated Version of an ADP-Glucose Pyrophosphorylase Promoter from Potato Specifies Guard Cell-Selective Expression in Transgenic Plants", *The Plant Cell*, May 1994, vol. 6, pp. 601-612.
M. Ohto and K. Nakamura, "Sugar-Induced Increase of Calcium-Dependent Protein Kinases Associated with the Plasma Membrane in Leaf Tissues of Tobacco", *Plant Physiol.*, 1995, vol. 109, pp. 973-981.

* cited by examiner

*Primary Examiner*—Anne Marie Grunberg
*Assistant Examiner*—Brent Page
(74) *Attorney, Agent, or Firm*—Sughrue Mion, PLLC

(57) ABSTRACT

Disclosed herein are a novel sucrose-inducible promoter sequence and a 5' untranslated region which are derived from sweetpotato ADP-glucose pyrophosphorlyase gene (ibAGP1) (SEQ ID NO: 1). Also disclosed are expression vectors using the same sequences and a transgenic plant using the same vectors. The promoter and 5' untranslated region according to the present invention can confer a high level of sucrose-inducible expression in plants, particularly in plant storage roots which contain sucrose in relatively large quantities to accumulate starch in large quantities in plants. Therefore the present invention may be useful for the generation of transgenic plants to produce useful proteins in large quantities in plant storage roots.

11 Claims, 3 Drawing Sheets
(1 of 3 Drawing Sheet(s) Filed in Color)

[Fig. 1]

```
-1908
ACTGATACTTTGGTGACTGCATTGTGTTTGGGTCTTGCCAAATCTATTGAGGGAGGGGAAGAAAGTAGAA
GTGTCAGGGATTGGTGTGTGGTGGGGTTTCCAAAGTTTCCCTCTTTTCCTTTCTTATTCTTAGTTTGCTC
GTCATAAGTGTCAGGGATTGGTAACCAATAGAAATCTCATCTTTAACCTATATGTATGTTCTAGTATCAT
AATTAAGCTCTTACTCAAAGGAATGTTCCATTTAGGTCATTTTAATGTCTATCAATTGATCATTTCAAG
TAAACAAAACTCTGGCTCTAATGCTGGGACTTTGGTTTCTTTATTATGCAGTNTTATGGGATAAAGGTTG
GTTATGGTGGCATCCCGGGGCCATCAATCGGAAGAGATGGAGCTCCTGCTCCAGGAGGGGGTTGCTGCAG
CTGAAAATGGGACGTAATTTCTTTTGAGTAAATGCTTGTTTCATTGTNAATTCGTGACTAATTGTTCTTT
GTTTTTCAATTGTTCAAAAGCTTACTATGTATACGTGGTGTATAATGTAATACAACAGCCAGCATTAGGA
TGNAATAGAGGTTTCAAATTAAACTCAACCAGAATCCTGCTTATTTCGAGAATTACTACCATTCTCAAAA
AATAAATAAATAAATCATGAGATGTGTTGATATAAATAAATAAATCATGAGATGTGTTGAACGCTCTTCA
AGTTTTTCACAGTTGTATGAATAATGACGAGCACATGATAGTTAGAGAACTTAGGAGCATTGAATCTGGT
GCTTGGGCTGATCGATTTATGGCATGATGCAGTGCATTCACTGTATAGCGTGTGATTGCAGGCATTAGAT
CTTGGTTTATGGTCTGCATTTCACGTGGGGTGACCATTTTGTGCCGTTTCCGTCAGCCACTTAAATGGAC
CAACATCCCCTGAGGAAGACCTGCAAATTCAGACTTAGACACACTAATTATAGGGCATATGATATTATG
ATTGGATAATGGCTGATGAAATTTTCAGCCGTTAATTCTAAACAATAAACAGTATGGCGGTCTATGAATG
ATAACGATCTTTAAGCTGAAGATGGGCAAAACAATATGGATCGTCTACTAGTATTTGTCTCTTTCCCTAT
CCTGCTTGTCTACACCACAATACTAAAGACCAAAACTTGAGTGACTGAGAGAAATATGCATTCATTATCC
GAGTCTGTATCATGTAAATTTTATCTTGTAATTTTAACTAATAAAAAATCAGGAGAAAATCAGCCTAAAT
TATTTATAGCTCATAACTTACTAGTTCAGACTAAGAAGACTAATAAAACATCCCCGTTACAAAATTAACA
TTTTGACTAACTTGTAACGTTTGCATGGTCAGAAACAGGATACACCAACTTTGGTTGTGATGATGATATC
ATATCATAAACAAACCCTCCAAAAAGTCACTTGCAAGGTGGCACTTTGCGACAGACCACCATGCTTAATT
GCTCATAATCAGCTAAACTATTATTATTACTTTATAAAATATTTTCGCCCCATATCATATAATTTGGCCA
ATAATATATCATTTTATCTGTCTTACTTATTATTTATTAATTACATAAAATGAAACGGAATGAATAACAT
AAATAATATAAAGATATACTCCGTATAAGTAACGGTGCAAAGGAGCCGATTAGATATTTTCAGTAATCAC
AAGTCACATGTGATCATATCATGTGTATTTTCATATAAAATAAAACTAGTATACCCCACCCTGATTTTT
GCTCTAAACTTCCAAATATACCCTTGGTCACGCAAATGCTAGCCGCTGGTTTGGAAGGGCAAACCGTAAA
TGTTGACAAATTCTTTGGCAATTAGGTAATAGGTGTCACCTATTTGAACACTTACTATAAAAGGACGCCT
AGTTTCTGTCCAAATTTC
+1
AACAGAATCACTCGCTTCCACACACTCCAAAGTCCGCAGAGAGCTCAGAGTGGTAGCGCGGCTTAAAAATG
```

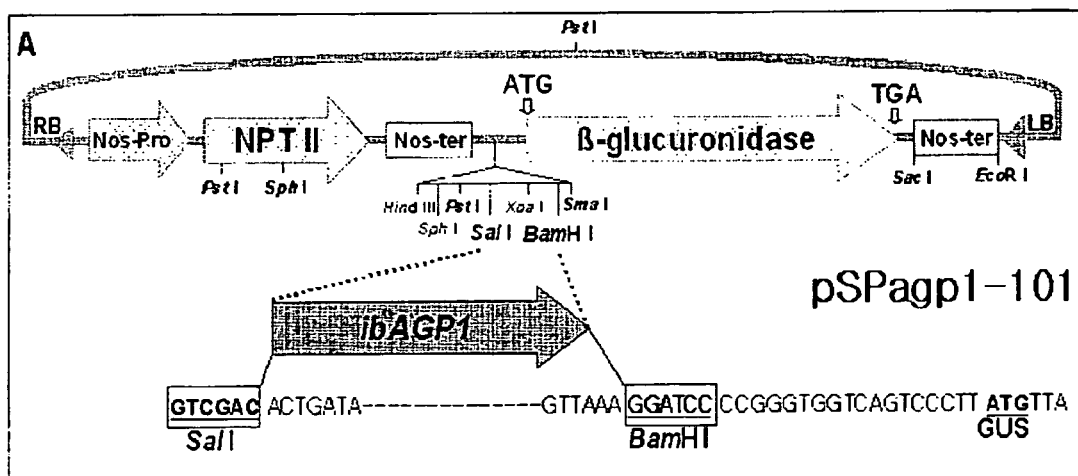

[Fig. 2]

[Fig. 5]
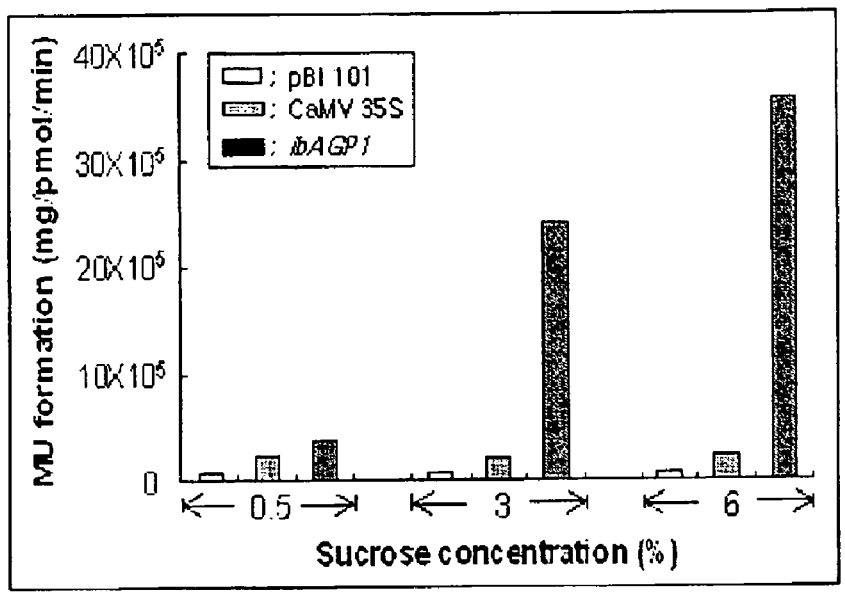
[Fig. 6]
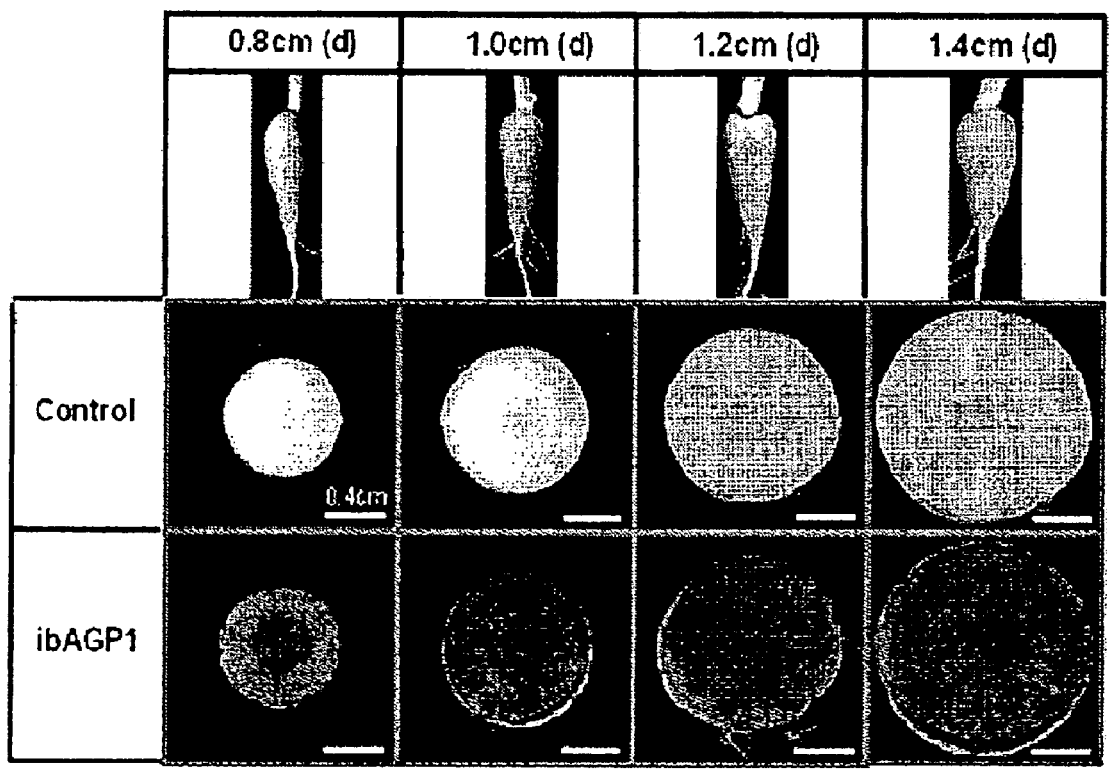

SEQUENCE LISTING

<160> NUMBER OF SEQ ID NOS: 5

<210> SEQ ID NO 1
<211> LENGTH: 1979
<212> TYPE: DNA
<213> ORGANISM: Ipomoea batatas cv Yumli
<220> FEATURE:
<221> NAME/KEY: n
<222> LOCATION: 333..333
<223> OTHER INFORMATION: Unknown
<220> FEATURE:
<221> NAME/KEY: n
<222> LOCATION: 468..468
<223> OTHER INFORMATION: Unknown
<220> FEATURE:
<221> NAME/KEY: n
<222> LOCATION: 563..563
<223> OTHER INFORMATION: Unknown

<400> SEQUENCE: 1
actgatactt tggtgactgc attgtgtttg ggtcttgcca aatctattga gggaggggaa      60
gaaagtagaa gtgtcaggga ttggtgtgtg gtggggtttc caaagtttcc ctctttttcct    120 ttcttattct tagtttgctc gtcataagtg tcagggattg gtaaccaata gaaatctcat    180 cttttaaccta tatgtatgtt ctagtatcat aattaagctc ttactcaaag gaatgttcca    240
tttaggtcat ttttaatgtc tatcaattga tcatttcaag taaacaaaac tctggctcta    300
atgctgggac tttggtttct ttattatgca gtnttatggg ataaaggttg gttatggtgg    360
catcccgggg ccatcaatcg gaagagatgg agctcctgct ccaggagggg gttgctgcag    420
ctgaaaatgg gacgtaattt cttttgagta aatgcttgtt tcattgtnaa ttcgtgacta    480
attgttcttt gttttcaat tgttcaaaag cttactatgt atacgtggtg tataatgtaa    540
tacaacagcc agcattagga tgnaatagag gtttcaaatt aaactcaacc agaatcctgc    600
ttatttcgag aattactacc attctcaaaa aataaataaa taaatcatga gatgtgttga    660
tataaataaa taaatcatga gatgtgttga acgctcttca agttttttcac agttgtatga    720 ataatgacga gcacatgata gttagagaac ttaggagcat tgaatctggt gcttgggctg    780
atcgatttat ggcatgatgc agtgcattca ctgtatagcg tgtgattgca ggcattagat    840
cttggtttat ggtctgcatt tcacgtgggg tgaccatttt gtgccgtttc cgtcagccac    900
ttaaatggac caacatcccc tgaggaagac ctgcaaattc agacttagac acactaatta    960 tagggggcata tgatattatg attggataat ggctgatgaa attttcagcc gttaattcta   1020
aacaataaac agtatggcgg tctatgaatg ataacgatct ttaagctgaa gatgggcaaa   1080
acaatatgga tcgtctacta gtatttgtct cttcccctat cctgcttgtc tacaccacaa   1140
tactaaagac caaaacttga gtgactgaga gaaatatgca ttcattatcc gagtctgtat   1200
catgtaaatt ttatcttgta attttaacta ataaaaaatc aggagaaaat cagcctaaat   1260
tatttatagc tcataactta ctagttcaga ctaagaagac taataaaaca tcccggtaac   1320
aaaattaaca ttttgactaa cttgtaacgt ttgcatggtc agaaacagga tacaccaact   1380
ttggttgtga tgatgatatc atatcataaa caaaccctcc aaaaagtcac ttgcaaggtg   1440
gcactttgcg acagaccacc atgcttaatt gctcataatc agctaaacta ttattattac   1500
tttataaaat attttcgccc catatcatat aatttggcca ataatatatc attttatctg   1560
tcttacttat tatttattaa ttacataaaa tgaaacggaa tgataacat aaataatata    1620 aagatatact ccgtataagt aacggtgcaa aggagccgat tagatatttt cagtaatcac   1680

```
aagtcacatg tgatcatatc atgtgtattt tcatataaa ataaaactag tataccccac    1740
cctgattttt gctctaaact tccaaatata cccttggtca cgcaaatgct agccgctggt    1800
ttggaagggc aaaccgtaaa tgttgacaaa ttctttggca attaggtaat aggtgtcacc    1860
tatttgaaca cttactataa aaggacgcct agtttctgtc caaatttcaa cagaatcact    1920
cgcttccaca cactccaaag tccgcagaga gctcagagtg gtagcgcggc ttaaaaatg    1979

<210> SEQ ID NO 2
<211> LENGTH: 27
<212> TYPE: DNA
<213> ORGANISM: Artificial Sequence
<220> FEATURE:
<223> OTHER INFORMATION: Primer for PCR

<400> SEQUENCE: 2
cgagtcgaca ctgatacttt ggtgact                                         27

<210> SEQ ID NO 3
<211> LENGTH: 27
<212> TYPE: DNA
<213> ORGANISM: Artificial Sequence
<220> FEATURE:
<223> OTHER INFORMATION: Primer for PCR

<400> SEQUENCE: 3
tgcggatcct tttaagccgc gctacca                                         27

<210> SEQ ID NO 4
<211> LENGTH: 27
<212> TYPE: DNA
<213> ORGANISM: Artificial Sequence
<220> FEATURE:
<223> OTHER INFORMATION: Primer for PCR

<400> SEQUENCE: 4
cgcgcatgca ctgatacttt ggtgact                                         27

<210> SEQ ID NO 5
<211> LENGTH: 27
<212> TYPE: DNA
<213> ORGANISM: Artificial Sequence
<220> FEATURE:
<223> OTHER INFORMATION: Primer for PCR

<400> SEQUENCE: 5
tgcggatcct tttaagccgc gctacca                                         27
```

SUCROSE-INDUCIBLE PROMOTER FROM SWEETPOTATO

This is a national stage application under 35 U.S.C. § 371 of PCT/KR2005/002820 filed on Aug. 25, 2005, which claims priority from Korean patent application 10-2004-0070820 filed on Sep. 6, 2004, all of which are incorporated herein by reference.

TECHNICAL FIELD

The present invention relates to a plant sucrose-inducible promoter sequence. More specifically, the present invention relates to a plant sucrose-inducible promoter sequence which originates from sweetpotato ADP-glucose pyrophosphorylase gene (ibAGP1) and can confer a high level of sucrose-inducible expression in plants. In addition, the present invention relates to plant sucrose-inducible expression vectors comprising the promoter sequence, and to production of a transgenic plant using the promoter sequence.

BACKGROUND ART

Molecular breeding technology for crops makes it possible to use the genes of all species as breeding material and to regulate the effects of breeding minutely at the gene level instead of at the genome level as in the past. Therefore it is one of the core technologies leading into the next generation of agriculture.

In order to maximize the effects of such molecular breeding technologies for crops, the essential prerequisites are as follows:

1) The accumulation of a database of genes to represent various plants;
2) The establishment of transformation systems for various crops; and
3) The development of promoters that regulate the expression of foreign genes inserted into plants.

In foreign countries promoters regulating the expression of plant genes have been studied since the early 1980's. It has been suggested that a promoter of cauliflower mosaic virus could induce high levels of gene expression in all kinds of plant tissues (Hohn et al., 1982, Cwrr. *Topics Microbiol. Immunol.* 96: 193-236).

Subsequently, the sequence of the promoter was identified (Odell et al., 1985, *Nature* 313:810-812). It was proven that the promoter could induce high levels of gene expression in plants (Sanders et al., 1987, *Nucleic Acids Res.* 15: 1543-58). Since then, CaMV 35S promoter (Patent NO.: JP1993192172-A1) has become the most universal promoter used in plants.

Since the identification of CaMV 35S, other inducible promoters whose activities increase under biotic or abiotic conditions have been actively studied.

Especially, sucrose-inducible promoters whose activities increase upon treatment with sucrose have been actively studied. Such sucrose-inducible promoters have merits when applied to the mass production of useful medicinal and industrial proteins in plant storage organ tissues, such as storage roots, which contain starch synthesized from sucrose in relatively large quantities. Such useful proteins include very valuable and expensive medicinal or industrial proteins, such as interferon, growth hormones, Lactoferrin, and phytase.

The studies on sucrose-inducible promoters have been focused on genes coding storage proteins accumulated in storage organ tissues or genes relating to the synthesis of starch.

For example, patatin is a storage protein in the potato. It has been identified that the activity of a patatin gene promoter is increased by sucrose (Rocha-Sosa et al., 1989, EMBO J 8, 23-31; Wenzler et al., 1989a, Plant Mol. Biol. 12, 41-50; Wenzler et al., 1989b, Plant Mol. Biol. 13, 347-354). It has also been reported that a specific nucleotide sequence of the −344 region of the promoter (B sequence) plays an essential role in sucrose induction (Grierson et al., 1994, Plant J, 5, 815-826).

Meanwhile, there are two sucrose synthase genes, Sus3 and Sus4, in the potato. It has been identified that Sus4, among the two genes, is expressed by sucrose (Salanoubat and Belliard, 1989, GENE 84, 181-185). In addition, it has been reported that the −1500~−267 region of the Sus4 gene promoter, the 3' untranslated region, and a 1612 bp leader intron are essential for sucrose induction (Fu et al., 1995, Plant Cell 7, 1387-1394).

Furthermore, it has been identified that the activity of a starch-branching enzyme I (SBE1) gene promoter in corn is increased by sucrose, and that a sequence between −314 and −145, relative to the transcription initiation site of the gene, is essential for sucrose induction (Kim and Guiltinan, 1999, Plant Physiology 121, 225-236).

In addition, it has been reported that the activity of a β-amylase gene promoter in sweetpotato is inducible by sucrose and that a sequence between −901 and −820, relative to the transcription initiation site of the gene, is essential for sucrose induction. Furthermore, a TGGACGG sequence therein plays an important role as a regulator (Maeo et al., 2001, Plant Mol. Biol. 46, 627-637).

Meanwhile, ADP-glucose pyrophosphorlyase is believed to be the key regulatory enzyme in controlling the amount of starch in plants. The ADP-glucose pyrophosphorlyase gene promoters in tomato and *Arabidopsis* have been reported to be sucrose-inducible (Siedlecka et al., 2003, Planta 217, 184-192; Li et al., 2002, Plant Science 162, 239-244). In addition, it has been reported that the activity of the promoter in *Arabidopsis* is decreased by okadaic acid, which is an inhibitor of protein phosphatase I and 2A.

Meanwhile, there are two ADP-glucose pyrophosphorlyase genes, ibAGP1 and ibAGP2, in sweetpotato. It has been reported that the expression of the ibAGP1 gene (the gene was previously named ibAGP-sTL1) is enhanced by sucrose (Bae and Liu, 1997, Molecular Genetics and Genomics 154, 179-185). The full nucleotide sequences of the above two genes have been analyzed and compared, and the transcription initiation site of each of the genes has been identified (Noh et al., in press, GENE).

However, nucleotide sequence of highly efficient sucrose-inducible promoter has not been reported. Therefore, there is an increasing need for sucrose-inducible promoters that can play important roles in the cheap and efficient production of useful foreign proteins in large quantities in plants.

DISCLOSURE OF INVENTION

Technical Problem

In order to solve the above problems and needs, an object of the present invention is to provide a sucrose-inducible promoter sequence that can induce a high level expression of target genes and that is derived from the sweetpotato ADP-glucose pyrophosphorlyase gene (ibAGP1) (SEQ ID NO: 1).

Another object of the present invention is to provide a sucrose-inducible vector for plant transformation comprising the sucrose-inducible promoter sequence directing a high level of expression of target genes and a 5' untranslated region of the ibAGP1 gene.

A still further object of the present invention is to provide a transgenic plant transformed with the same vector, capable of producing useful materials in large quantities in storage organ tissues of plants, such as in storage roots.

Technical Solution

In order to accomplish the above objects, the present inventors have cloned a sucrose-inducible promoter region of the sweetpotato ADP-glucose pyrophosphorlyase gene (ibAGP1) and constructed a vector for plant transformation and a transient expression vector comprising the above promoter with the 5' untranslated region of the same gene. These inventors have subsequently induced expression in the storage roots using the same vectors, and observed a high level of activity of the promoter with regard to sucrose inducibility to accomplish the present invention.

Therefore, the present invention provides the isolated DNA sequence of the sucrose-inducible promoter region and the 5' untranslated region of the sweetpotato ADP-glucose pyrophosphorlyase gene (ibAGP1) comprising the sequences of SEQ ID NO: 1.

The above DNA sequence of the promoter is derived from the region of bp −1 to −1908 relative to the transcription initiation site of the sweetpotato ADP-glucose pyrophosphorlyase gene (ibAGP1) in SEQ ID NO: 1 (see FIG. 1). The high levels of activity of the promoter according to the present invention can be induced by sucrose in plants.

The above untranslated region comprises the untranslated region of bp +1 to +68 relative to the transcription initiation site of the sweetpotato ADP-glucose pyrophosphorlyase gene (ibAGP1) in SEQ ID NO: 1 (see FIG. 1). The untranslated region according to the present invention possibly can induce a high level of expression of the target gene, like the other reported 5' untranslated regions of plants, by enhancing the translation efficacy of a target foreign gene introduced into the plant.

In order to accomplish another object, the present invention provides a sucrose-inducible vector for plant transformation (pSPagp1-101) and a transient expression vector (pSPagp 1-221), comprising a plant sucrose-inducible promoter directing high levels of expression in plants and a 5' untranslated region of the sweetpotato ADP-glucose pyrophosphorlyase gene (ibAGP1).

The above sucrose-inducible vector for plant transformation means a binary vector that can permanently express foreign genes in transgenic plants. The above transient expression vector means a vector that can transiently express foreign genes in plants.

The binary vector can be any binary vector comprising the RB and LB of T-DNA that can transform the plant in the presence of the Ti plasmid of Agrobacterium tumefaciens. Preferably, it may be a binary vector frequently used in the related field, such as the pBI101 (cat#: 6018-1, Clonetech, USA), pBIN (Genbank accession NO. U09365), pBI121, pBIN20, or BIBAC vectors.

Concerning the sucrose-inducible vectors (pSPagp 1-101, pSPagp 1-221) for plants according to the present invention, the promoter and 5' untranslated region of ADP-glucose pyrophosphorlyase gene (ibAGP1) according to the present invention are located in front of the foreign gene in pBI101 and pBI221. The present invention provides pSPagp1-101 and pSPagp1-221 (see FIGS. 2 and 3) prepared by inserting the promoter and 5' untranslated region of ADP-glucose pyrophosphorlyase gene (ibAGP1) according to the present invention into the vector (pBI101 and pBI221) including the GUS reporter gene. However, the GUS reporter gene is a foreign gene, and is expected to be replaceable with any other useful foreign gene.

The present invention provides a transgenic plant using the sucrose-inducible binary vector according to the present invention. Further the present invention provides a storage root transiently transformed using the transient expression vector according to the present invention.

Plants can be transformed with the above plant sucrose-inducible binary vector using, for example, Agrobacterium tumefaciens (An, G. 1987, Plant Physiology) or the method of particle bombardment (Lacorte et al., 1997, Plant Cell Reports). In the present invention, for example, Arabidopsis is transformed using the floral dip method (Clough and Bent, 1998, Plant J.). Plant storage roots can be transiently transformed using the transient expression vector, according to the present invention, and the particle bombardment method. The transient expression vector of the present invention can transform storage roots regardless of the kind of crop. Examples of crops include carrots, etc.

The above foreign gene may be any gene that is intended to be expressed in large quantities in plant storage organ tissues which contain sucrose in relatively large quantities to accumulate starch in large quantities in the plant. Furthermore, the foreign genes are located next to the promoter and 5' untranslated region of the sweetpotato ADP-glucose pyrophosphorlyase gene (JbAGP1) in the plant sucrose-inducible vector according to the present invention and may be expressed in the form of being fused with the reporter genes if necessary.

The present invention provides PCR primers of SEQ ID NO: 2~SEQ ID NO: 5 suitable for amplifying DNA fragment of plant sucrose-inducible promoter according to the present invention.

Advantageous Effects

The present invention provides a sucrose-inducible promoter and 5' untranslated region of the ADP-glucose pyrophosphorlyase gene (JbAGP1) from sweetpotato (Ipomoea batatas). The promoter and 5' untranslated region according to the present invention can confer sucrose-inducible expression in plants, and, particularly, can confer high levels of expression in plant storage roots which contain sucrose in relatively large quantities to accumulate starch in large quantities in the plants.

Therefore, the present invention may be useful for the generation of transgenic plants to produce useful proteins in large quantities in plant storage roots. Such useful proteins include very valuable and expensive medicinal or industrial proteins, such as interferon, growth hormones, Lactoferrin, and phytase.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

The above and other objects, features and other advantages of the present invention will be more clearly understood from the following detailed description taken in conjunction with the accompanying drawings, in which:

FIG. 1 shows DNA sequences of a plant sucrose-inducible promoter and a 5' untranslated region of the sweetpotato ADP-glucose pyrophosphorlyase gene (ibAGP1) according to the present invention, the DNA sequence is being included as SEQ ID NO:1 in the Sequence Listing;

FIG. 2 shows a diagrammatic representation of a binary vector for plant transformation (hereinafter referred to as 'pSPagp1-101') comprising sequences of plant sucrose-inducible promoter and a 5' untranslated region of the sweetpotato ADP-glucose pyrophosphorlyase gene (JbAGP1) according to the present invention;

FIG. 3 shows a diagrammatic representation of a transient expression vector (hereinafter referred to as 'pSPagp1-221') comprising sequences of a plant sucrose-inducible promoter and a 5' untranslated region of the sweetpotato ADP-glucose pyrophosphorlyase gene (JbAGP1) according to the present invention;

FIG. 5 shows the results of quantitative analysis of GUS after sucrose treating of *Arabidopsis* transformed with the pSPagp1-101; and FIG. 6 shows results of transient assay with carrot taproots using pSPagp 1-221 according to the present invention.

BEST MODE FOR CARRYING OUT THE INVENTION

Figure 4:
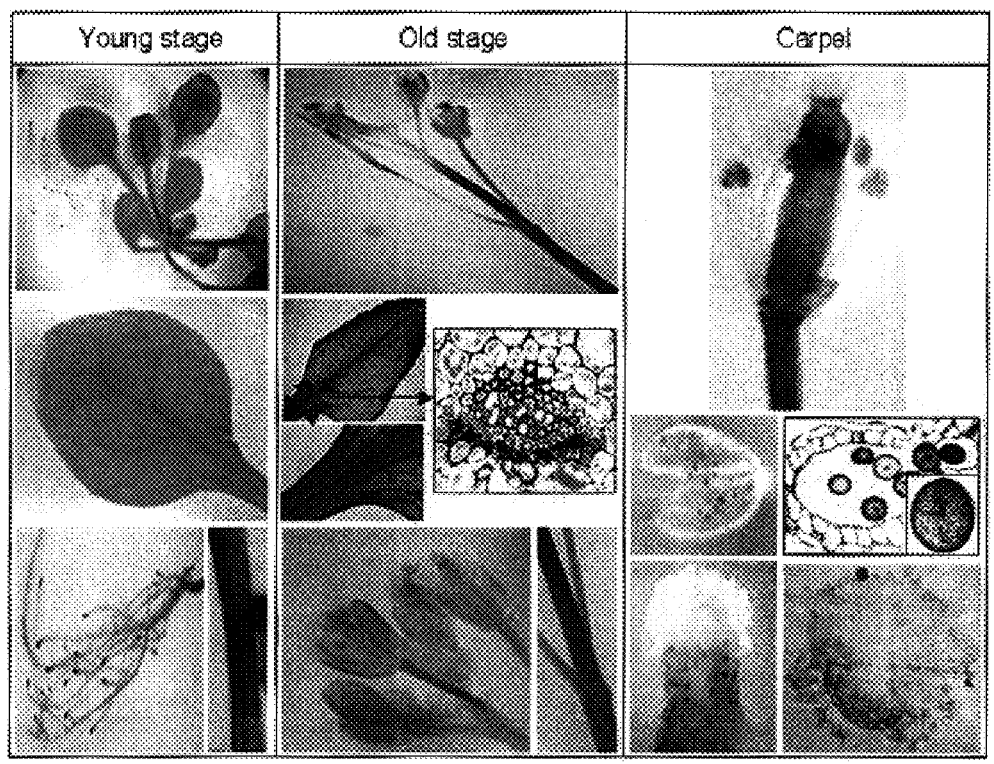
FIG. 4 shows GUS expression patterns of each tissue observed after histochemical staining of *Arabidopsis* transformed with the pSPagp1-101.

The following examples will enable those skilled in the art to more clearly understand how to practice the present invention. It is to be understood that, while the invention has been described in conjunction with the preferred specific embodiments thereof, that which follows is intended to illustrate, not to limit the scope of the invention. Other aspects of the invention will be apparent to those skilled in the art to which the invention pertains.

EXAMPLE 1

Cloning of the Sucrose-inducible Promoter of the Sweetpotato ADP-glucose Pyrophosphorlyase Gene (ibAGP1)

A promoter of the sweetpotato ADP-glucose pyrophospho-rlyase gene (ibAGP1) was identified in the 5' region sequence of the sweetpotato ADP-glucose pyrophosphorlyase gene (ibAGP1, Noh et al., *GENE*, 2004, 339, 173-180).

The 1,908 bp sequence of the cloned promoter was registered in NCBI GenBank (Accession no. AY694185, FIG. 1). FIG. 1 shows DNA sequences of a plant sucrose-inducible promoter and a 5' untranslated region of the sweetpotato ADP-glucose pyrophosphorlyase gene (ibAGP1) according to the present invention. In FIG. 1, the start codon 'ATG' of protein synthesis is underlined and in bold type, and the base 'A' of the translation initiation site is indicated by '+1A'

EXAMPLE 2

Construction of Plant Sucrose-inducible Vector and a Transient Expression Vector The sweetpotato ADP-glucose pyrophosphorlyase gene (ibAGP1) promoter cloned in example 1 and a 68 bp 5' untranslated region (SEQ NO ID: 1, FIG. 1) were inserted into pBHO1 or pBI221 (Clonetech) to construct a plant sucrose-inducible vector or a transient expression vector respectively.

More specifically, in the case of the construction of a plant sucrose-inducible vector, the sweetpotato ADP-glucose pyrophosphorlyase gene (ibAGP1) promoter, cloned in example 1, and a 68 bp 5' untranslated region (SEQ NO ID: 1, see FIG. 1) were amplified by PCR and digested with Sai1 and BamHI. Then they were inserted into the Sai1 and BamHI sites of pBHO1. The vector was termed as pSPagp1-101 (see FIG. 2). The primers used in the above PCR are shown in Table 1 in detail.

For PCR amplification, after incubation for 4 min at 94° C., the following cycling parameters were used; 30 cycles [94° C. for 1 min; 55° C. for 1 min; and 72° C. for 1.5 min]. Then, the reaction was incubated for 10 min at 72° C.

TABLE 1

| | |
|---|---|
| 5' Primer | 5'-CGAGTCGACACTGATACTTTGGTG SEQ ID NO: 2 ACT-3' |
| 3' Primer | 5'-TGCGGATCCTTTTAAGCCGCGCTA SEQ ID NO: 3 CCA-3' |

In FIG. 2, GUS is a reporter gene which encodes β-glucuronidase and selectable marker is kanamycin. In addition, Nos-pro represents a promoter of NPTII and Nos-ter represents a terminator thereof. The GUS reporter gene is expressed by an inserted promoter and terminator (Nos-ter) of Nos (Nopalin synthase) in plants.

In the case of the construction of a plant sucrose-inducible transient expression vector, the sweetpotato ADP-glucose pyrophosphorlyase gene (ibAGP1) promoter, cloned in example 1, and a 68 bp 5' untranslated region (SEQ NO ID: 1, see FIG. 1) were amplified by PCR and digested with Sph1 and BamHI. Then they were inserted into the Sph1 and BamHI sites of pBI221. The vector was termed as pSPagp 1-221 (see FIG. 3). The primers used in the above PCR are shown in Table 2 in detail.

For PCR amplification, after incubation for 5 min at 94° C., the following cycling parameters were used; 30 cycles [94° C. for 1 min; 58° C. for 1 min; and 72° C. for 1.5 min]. Then, the reaction was incubated for 5 min at 72° C.

TABLE 2

| | |
|---|---|
| 5' Primer | 5'-CGCGCATGCACTGATACTTTGGTG SEQ ID NO: 4 ACT-3' |
| 3' Primer | 5'-TGCGGATCCTTTTAAGCCGCGCTA SEQ ID NO: 5 CCA-3' |

EXAMPLE 3

Transformation of *Arabidopsis* using the pSPagp1-101 Vector Constructed in Example 2

The pSPagp1-101 vector constructed in Example 2 was transferred to *Agrobacterium tumefaciens* C58C1 using the Freeze-thaw method (An, G. 1987, Methods in Enzymology).

The transformed *Agrobacteria* were incubated in a shaking incubator for 2 days at 28° C. and were inoculated in the pistil of *Arabidopsis thaliana* cv. Columbia right before the blooming stage to produce the transformed *Arabidopsis* plant using a floral dip method (Clough and Bent, 1998, The Plant Journal).

EXAMPLE 4

Histochemical Staining and Enzymological Assay of Transformed *Arabidopsis*

The seeds of the *Arabidopsis thaliana* transformants in Example 3 were harvested and placed on the MS growth medium containing 30 mg/L of kanamycin in order to screen the resistant transgenic plant.

The GUS activity of all tissues of screened *Arabidopsis* transformants was examined quantatively using the methods of histochemical staining and enzymology. In order to stain all of the tissues of the transformed plants, each tissue was soaked in a solution containing 1 mM G-glu (5-bromo-4-chloro-3-indolyl-β glucuronide), 10 OmM sodium phosphate (pH 7.0), 1 OmM EDTA, 0.5 mM potassium ferricyanide, 0.5 mM potassium ferrocyanide, and 0.1% Triton X-100, and reacted for 12 hours at 37° C. After the solution was removed, the tissues were rinsed with series of ethanol (70-100%) to remove the chlorophyll contained in the tissues.

As shown in FIG. 4, high levels of GUS activity were identified in leaves, phloems, flower stalks and root apical meristems of *Arabidopsis* transformed with pSPagp1-101 and low levels of GUS activity were identified in pollen thereof.

EXAMPLE 5

Identification of the Activity of the Sucrose-inducible Promoter (ibAGP1 Promoter) According to the Present Invention In order to identify the sucrose-inducible activity of the ibAGP1 promoter, the GUS activity was examined quantitatively with sucrose-treated transformed *Arabidopsis* using the method of Jefferson et al., (EMBO J. 6: 3901-3907, 1987).

More specifically, the seeds of *Arabidopsis thaliana* transformants were sown on the MS growth medium containing 0.5%, 3% and 6% sucrose and were incubated for 14 days.

Incubated seedlings were then harvested and were ground with a solution containing 5 OmM sodium phosphate (pH 7.0), 1 OmM EDTA, 0.1% Triton X-100, 0.1% sodium lauroylsarcosine, and 1 OmM β-mercaptoethanol and were centrifuged at 12,000×g to obtain the supernatant.

The obtained supernatant was reacted with ImM MUG (4-methylumbelliferyl glucuronide) at 37° C. The reaction was stopped by the addition of 0.2M $Na_2CO_3$. The fluorescence of the resultant reaction solution was measured at 365 nm and 455 nm using a fluorometer. By comparison between the fluorescence of a reaction solution and the normal curve of a MUG standard solution, the GUS activity in the *Arabidopsis* transformants was analyzed and is shown in FIG. 5.

The GUS activity shown in FIG. 5 was obtained by analyzing the twelve transformants (T2 line plant) treated with each sucrose concentration. For comparison, the pB1O1 vector without the promoter and pB121 (Clonetech, USA) with the CaMV35S promoter were examined together. The results revealed that the GUS activity of the ibAGP1 gene promoter increased 8 times upon treatment with 3% sucrose, and increased 11 times upon treatment with 6% sucrose. In addition, the GUS activity of the ibAGP1 gene promoter increased 12-15 times compared to the universal promoter, CaMV35S.

EXAMPLE 6

Identification of the Activity of the Sucrose-inducible Promoter (ibAGP1 Promoter) in Carrot Taproots In order to identify the activity of the sucrose-inducible promoter (ibAGP1 promoter) in plant storage roots, the transient assay method was carried out using pSPagp 1-221 constructed in Example 2.

More specifically, the taproots of carrot in growth and enlargement stages were picked and washed. Then the taproots were transversely cut to 5 mm thick and placed on fully wet 3 MM paper in Petri dishes for 4-5 hours at 4° C.

According to the method of Sanford et al. (1993, Meth Enzymol 217:485-509), DNA was mixed and coated onto gold particles 1.0 μm in diameter. In this case, the following bombarding conditions were used; [1.0 μg DNA/bombardment, 1,350 PSi pressure of helium gas, and a distance of 6 cm from carrots]

After bombarding, they were placed in the darkness for 24 hours at 25° C. and histochemical staining was carried out to identify the activity of GUS. In order to stain the cut taproots of carrot, they were soaked in a solution comprising ImM X-glu (5-bromo-4-chloro-3-indoly-β-glucuronide) dissolved in DMSO (dimethyl sulfoxide), 10 OmM sodium phosphate (pH 7.0), 1 OmM EDTA, 0.5 mM potassium ferricyanide, 0.5 mM potassium ferrocyanide and 0.1% Triton X-100, and reacted for 24 hours at 37° C.

After the solution was removed, cut taproots were rinsed with 70% ethanol for 24 hours and were then placed in regularly changed 100% ethanol for a few days to remove the anthocyanin pigments contained in the tissues.

As shown in FIG. 6, it was identified that pSPagp 1-221 shows a high level of activity in all carrot taproot tissues, especially increasing in proportion to the diameter of taproot (increasing in proportion to the sucrose content).

If the above results are considered together, it can be said that promoter according to the present invention shows a high level of activity in plant storage organ tissues having high levels of sucrose content.

INDUSTRIAL APPLICABILITY

As described above, the present invention provides sucrose-inducible promoter and 5' untranslated region of sweetpotato ADP-glucose pyrophosphorlyase gene (ibAGP1).

The present invention provides the plant binary vector and the transient expression vector prepared by inserting the promoter and the 5' untranslated region into pBHO1 or pBI221, respectively.

Using the binary vector and transient expression vector, it has been identified that the promoter and 5' untranslated region of the sweetpotato ADP-glucose pyrophosphorlyase gene (JbAGP1) according to the present invention can confer sucrose-inducible expression, and particularly can confer high levels of expression in plant storage roots which contain sucrose in relatively large quantities to accumulate starch in large quantities in plants. Therefore, the present invention may be useful for the generation of transgenic plants to produce useful proteins in large quantities in plant storage roots. Also, the present invention may be useful for studies in areas such as the metabolic engineering of storage roots using transformants or the production of functional materials.

The invention claimed is:

1. An isolated plant sucrose-inducible promoter sequence, comprising the DNA nucleotide sequence of the bp −1 to −1,908 region of the sequence shown in FIG. 1, wherein the base position is relative to the transcription initiation site of SEQ ID NO: 1.

2. The isolated plant sucrose-inducible promoter sequence according to claim 1, wherein the said promoter sequence is from the ibAGP1 gene of sweetpotato ADP-glucose pyrophosphorylase.

3. An isolated 5' untranslated region of a sweetpotato ADP-glucose pyrophosphorlyase gene, comprising the nucleotide sequence of the bp +1 to +68 region of the sequence shown in FIG. 1, wherein the base position is relative to the transcription initiation site of SEQ ID NO: 1.

4. A sucrose-inducible binary vector for plant transformation, comprising a plant sucrose-inducible promoter sequence, comprising the DNA nucleotide sequence of the bp −1 to −1,908 region of the sequence shown in FIG. 1, wherein the base position is relative to a transcription initiation site of SEQ ID NO: 1; and a 5' untranslated region of a sweetpotato ADP-glucose pyrophosphorlyase gene, comprising the nucleotide sequence of the bp +1 to +68 region of the sequence shown in FIG. 1, wherein the base position is relative to the transcription initiation site of SEQ ID NO: 1.

5. A sucrose-inducible transient expression vector for plants, comprising a plant sucrose-inducible promoter sequence, comprising the DNA nucleotide sequence of the bp −1 to −1,908 region of the sequence shown in FIG. 1, wherein the base position is relative to the transcription initiation site of SEQ ID NO: 1; and a 5' untranslated region of a sweetpotato ADP-glucose pyrophosphorlyase gene, comprising the nucleotide sequence of the bp +1 to +68 region of the sequence shown in FIG. 1, wherein the base position is relative to the transcription initiation site of SEQ ID NO: 1.

6. An *E. coli* carrying the sucrose-inducible binary vector claim 4.

7. An *E. coli* carrying the transient expression vector of claim 5.

8. A transgenic plant transformed with a binary vector comprising the plant sucrose-inducible promoter sequence, comprising the DNA nucleotide sequence of the bp −1 to −1,908 region of the sequence shown in FIG. 1, wherein the base position is relative to the transcription initiation site of SEQ ID NO: 1; and a 5' untranslated region of a sweetpotato ADP-glucose pyrophosphorlyase gene, comprising the nucleotide sequence of the bp +1 to +68 region of the sequence shown in FIG. 1, wherein the base position is relative to the transcription initiation site of SEQ ID NO: 1.

9. The isolated promoter of claim 1, wherein the promoter is amplified by a primer pair represented by the sequences of SEQ ID NO:2 and 3.

10. The isolated promoter of claim 1, wherein the promoter is amplified by a primer pair represented by the sequences of SEQ ID NO:4 and 5.

11. A vector comprising a plant sucrose-inducible promoter sequence, said promoter sequence consisting of the DNA nucleotide sequence of the bp −1 to −1,908 region of the sequence shown in FIG. 1, wherein the base position is relative to a transcription initiation site of SEQ ID NO: 1; and a 5' untranslated region of a sweetpotato ADP-glucose pyrophosphorlyase gene, consisting of the nucleotide sequence of the bp +1 to +68 region of the sequence shown in FIG. 1, wherein the base position is being relative to the transcription initiation site of SEQ ID NO: 1.

\* \* \* \* \*